United States Patent
Fathi et al.

(10) Patent No.: US 11,219,639 B2
(45) Date of Patent: *Jan. 11, 2022

(54) ANTISEPTIC POLYMER AND SYNTHESIS THEREOF

(71) Applicant: Trimph IP Pty Ltd, Sydney (AU)

(72) Inventors: Ali Fathi, Paddington (AU); Fariba Dehghani, Killarney Heights (AU)

(73) Assignee: TRIMPH IP PTY LTD, Sydney (AU)

( * ) Notice: Subject to any disclaimer, the term of this patent is extended or adjusted under 35 U.S.C. 154(b) by 604 days.

This patent is subject to a terminal disclaimer.

(21) Appl. No.: 15/746,810

(22) PCT Filed: Jul. 22, 2016

(86) PCT No.: PCT/AU2016/050653
§ 371 (c)(1),
(2) Date: Jan. 23, 2018

(87) PCT Pub. No.: WO2017/015703
PCT Pub. Date: Feb. 2, 2017

(65) Prior Publication Data
US 2020/0078392 A1    Mar. 12, 2020

(30) Foreign Application Priority Data

Jul. 24, 2015 (AU) .............................. 2015902943

(51) Int. Cl.
| | |
|---|---|
| *A61K 31/60* | (2006.01) |
| *C08F 220/54* | (2006.01) |
| *C07C 65/10* | (2006.01) |
| *C08F 220/56* | (2006.01) |
| *C08L 33/26* | (2006.01) |
| *A61K 31/78* | (2006.01) |
| *A61K 47/58* | (2017.01) |
| *A61K 47/59* | (2017.01) |
| *A61K 47/61* | (2017.01) |
| *A61K 47/69* | (2017.01) |
| *A61K 47/60* | (2017.01) |
| *A61L 27/16* | (2006.01) |
| *A61L 27/52* | (2006.01) |
| *A61L 27/54* | (2006.01) |
| *A61L 27/58* | (2006.01) |

(52) U.S. Cl.
CPC .............. *A61K 31/78* (2013.01); *A61K 47/58* (2017.08); *A61K 47/593* (2017.08); *A61K 47/60* (2017.08); *A61K 47/61* (2017.08); *A61K 47/6903* (2017.08); *A61L 27/16* (2013.01); *A61L 27/52* (2013.01); *A61L 27/54* (2013.01); *A61L 27/58* (2013.01)

(58) Field of Classification Search
None
See application file for complete search history.

(56) References Cited

U.S. PATENT DOCUMENTS

| | | |
|---|---|---|
| 5,530,038 A | 6/1996 | Yamamoto et al. |
| 5,587,406 A | 12/1996 | Yamamoto et al. |
| 5,834,532 A | 11/1998 | Yamamoto et al. |
| 6,071,983 A | 6/2000 | Yamamoto et al. |
| 8,349,779 B2 * | 1/2013 | Scherer .............. C10M 169/044 508/469 |
| 2014/0357823 A1 | 12/2014 | Dehghani et al. |

FOREIGN PATENT DOCUMENTS

| | | |
|---|---|---|
| FR | 2 629 084 A1 | 9/1989 |
| JP | S64-11113 A | 1/1989 |
| JP | H02-8206 A | 1/1990 |
| JP | H07-97306 A | 4/1995 |
| JP | H08119822 A | 5/1996 |

(Continued)

OTHER PUBLICATIONS

Elvira, C., et al. "Incorporation of salicylic acid derivatives to hydrophilic copolymer systems with biomedical applications." Journal of Materials Science: Materials in Medicine 12.6 (2001): 535-542.*

Babazadeh, Mirzaagha, Ladan Edjlali, and Lida Rashidian. "Application of 2-hydroxyethyl methacrylate polymers in controlled release of 5-aminosalicylic acid as a colon-specific drug." Journal of Polymer Research 14.3 (2007): 207-213. (Year: 2007).*

PCT International Search Report and Written Opinion dated Aug. 24, 2016 in connection with PCT International Patent Application No. PCT/AU2016/050653, 14 pages.

Guan J et al., "Protein-Reactive, Thermoresponsive Copolymers with High Flexibility and Biodegradability," Biomacromolecules, 2008, vol. 9, pp. 1283-1292, Scheme 2, Abstract Only.

(Continued)

*Primary Examiner* — Bethany P Barham
*Assistant Examiner* — Peter Anthopolos
(74) *Attorney, Agent, or Firm* — Amster, Rothstein & Ebenstein LLP (57) ABSTRACT

According to the present invention there is provided a polymer comprising at least one antiseptic/analgesic/anti-inflammatory monomeric unit in conjunction with at least three further monomeric units, said three further monomeric units eliciting properties selected from the group consisting of: temperature activation, water solubility, mechanical strength, protein/polysaccharide bonding capacity, and combinations thereof. In particular, disclosed herein is a polymer, wherein: the water-soluble monomeric unit is a hydrophilic ethylene glycol (OEGMA) moiety; the mechanical strength-conferring monomeric unit is polylactide-co-2-hydroxy-ethyl-methyl acrylate (PLA/HEMA); the protein-reactive monomeric unit is an N-acryloxysuccinimide (NAS) moiety; and the thermosetting monomeric unit is an N-isopropyl acrylamide (NIPAAm) moiety. The anti-septic/analgesic/anti-inflammatory monomeric unit comprises a methacrylic ester derivative of salicylic acid (5-HMA or 4-HMA, or a combination thereof).

5 Claims, 5 Drawing Sheets

(56) References Cited

FOREIGN PATENT DOCUMENTS

| JP | 2004-182661 A | 7/2004 | |
|---|---|---|---|
| WO | 2013091001 A1 | 6/2013 | |
| WO | WO-2013091001 A1 * | 6/2013 | ............ C08F 220/54 |

OTHER PUBLICATIONS

Communication Supplementary European Search Report dated Feb. 12, 2019 in connection with European Patent Application No. 16829490.8.
Mahkam, M, "Novel pH-sensitive hydrogels for colon-specific drug delivery," Drug Delivery, vol. 17, No. 3, Feb. 9, 2010, pp. 158-163.
Davaran S et al., "Synthesis and characterization of methacrylic derivatives of 5-amino salicylic acid with pH-sensitive swelling properties," AAPS Pharmscitech, vol. 2, No. 4, Dec. 1, 2001, pp. 80-85.
Guan J et al., "Protein-Reactive, Thermoresponsive Copolymers with High Flexibility and Biodegradability," Biomacromolecules, 2008, vol. 9, pp. 1283-1292.
Australian Examination Report No. 1 dated Jun. 28, 2018 from Australian Patent Appln. No. 2016301103.
Australian Examination Report No. 2 dated Apr. 9, 2019 from Australian Patent Appln. No. 2016301103.
Australian Examination Report No. 3 dated Apr. 16, 2019 from Australian Patent Appln. No. 2016301103.
Australian Examination Report No. 1 dated Sep. 1, 2020 from Australian Patent Appln. No. 2019229341.
European Examination Report, Communication Pursuant to Article 94(3) EPC dated Aug. 5, 2020 from European Patent Appln. No. 16829490.8.
Japanese Examination Report dated Jul. 10, 2020 from Japanese Patent Appln. No. 2018-503480 (with English Tanguage machine translation attached).

* cited by examiner

ANTISEPTIC POLYMER AND SYNTHESIS THEREOF

CROSS-REFERENCE TO RELATED APPLICATIONS

This application is a U.S. national stage entry under 35 U.S.C. § 371 of PCT International Patent Application No. PCT/AU2016/050653, filed Jul. 22, 2016, which claims priority to Australian Provisional Patent Application No. 2015902943, filed Jul. 24, 2015, the contents of which are incorporated herein by reference in their entirety.

TECHNICAL FIELD

The present invention relates to polymers useful in biomedical applications. In particular, the invention relates to a novel polymer comprising up to five monomeric units tunable in their relative proportions so as to elicit desired clinical properties such as temperature activation, water solubility, mechanical strength, biocompatibility and analgesic/anti-inflammatory properties. The incorporation of sustained analgesic/anti-inflammatory properties within a biocompatible polymer of this type is both a goal of and a notable absence in the art.

Although the present invention will be described hereinafter with reference to its preferred embodiment, it will be appreciated by those skilled in the art that the spirit and scope of the invention may be embodied in many other forms.

BACKGROUND

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

Hydrogels are renowned for their practical applications in the fields of tissue engineering, wound healing and drug delivery. Upon the in vivo delivery of hydrogels, however, foreign body immune responses and chronic inflammation may lead to serious clinical complications. The physical addition of antiseptic/anti-inflammatory drugs within a hydrogel may also only elicit temporary effects due to the burst release of the drug at very early stages post-operation; once an initial burst of antiseptic is exhausted, infection can readily occur at a surgical site.

Accordingly, an appropriate starting point from which the present invention may be more completely assessed is the Applicant's own foregoing patent application, PCT/AU2012/001566 (WO 2013/091001), the disclosure of which is incorporated herein by reference in its entirety; a corresponding disclosure is made in the subsequent literature publication, *Biomaterials*, 35 (2014), pp. 5425-5435 (hereinafter, collectively, "P1").

P1 is aimed at developing cytocompatible and injectable naturally derived protein hydrogels with alterable/tunable gelation characteristics, favourable mechanical properties and structural stability for load-bearing applications. A thermoresponsive copolymer, poly(N-isopropylacrylamide-co-polylactide-2-hydroxyethyl methacrylate-co-oligo(ethylene glycol)monomethyl ether methacrylate ("PNPHO"), was functionalised with succinimide ester groups by incorporating an N-acryloxysuccinimide monomeric component. These ester groups were exploited to covalently bond PNPHO to different proteins with primary amine groups such as α-elastin and collagen in aqueous media. The incorporation of elastin through covalent bond formation with PNPHO in turn promoted structural stability, advantageous mechanical properties and live cell proliferation within the structure of the PNPHO-containing hydrogels.

The results obtained in P1 demonstrate that elastin-co-PNPHO solutions were injectable through fine gauge needles and converted to hydrogels in situ at 37° C. in the absence of any crosslinking reagent. By altering the PNPHO content and composition, the gelation time of these hydrogels could be finely tuned within the range of 2-15 minutes to ensure compatibility with surgical requirements. In addition, these hydrogels exhibited compressive moduli in the range of 40-145 kPa, which are substantially higher than those of previously-developed elastin-based hydrogels. These hydrogels were highly stable in the physiological environment with the evidence of 10 wt % mass loss after 30 days of incubation in a simulated environment.

Furthermore, this class of hydrogels was in vivo bioabsorbable due to the gradual increase of the lower critical solution temperature of the copolymer to above 37° C. as a result of the cleavage of polylactide from the PNPHO copolymer. Moreover, P1 demonstrates that more than 80% of the cells encapsulated in these hydrogels remained viable and the number of encapsulated cells increased over a period of at least five days. These unique properties marked elastin-co-PNHPO hydrogels as favourable candidates for a broad range of tissue engineering applications.

From a patentability perspective, the essential difference between P1 and the present invention is the presence of an antiseptic monomeric unit 2-hydroxy-5-N-methacrylamido-benzoic acid (5-HMA) and/or 2-hydroxy-4-N-methacrylamidobenzoic acid (4-HMA) in the latter. P1 discloses a polymer (i.e., "PNPHO") comprising the other four monomers. Significantly, however, P1 lacks any teaching that one should seek to augment the PNPHO polymer with 5-HMA, 4-HMA (or a combination thereof, or indeed any monomer that confers antiseptic properties). As such, P1 provides no apparent motivation for the skilled addressee to seek a PHPHO polymer augmented with an antiseptic moiety—much less, an antiseptic moiety capable of sustained release over a period corresponding to that of initial wound healing.

Moreover, any prior knowledge that upon the in vivo delivery of hydrogels, foreign body immune responses and chronic inflammation may lead to serious clinical complications could be argued to direct the skilled addressee away from the present invention. To this end, the inclusion of an antiseptic moiety is somewhat counterintuitive in that, as mentioned above, the physical addition of antiseptic/anti-inflammatory drugs to hydrogels is known to elicit only a only a temporary effect due to the burst release of the drugs at very early stages post-operation. From this, the skilled person would likely infer that a moiety conferring antiseptic properties over the healing period of a surgery, although desirous, was largely unattainable. As such, the accepted wisdom merely identifies the problem; it would appear to provide no indication as to how the skilled person should seek to address it. As such, the absence of a feasible antiseptic moiety within a hydrogel carrier has been identified as a known shortcoming of the art.

In the past, salicylic acid has been chemically bonded with different monomers, e.g., 3,5-di(acrylyloxymethyl)salicylic acid and 3-methyl-S-acrylyloxymethyl salicylic acid. However, at no time has a class of injectable salicylic acid-based thermosetting hydrogels been provided with the capacity to bond with natural and synthetic peptides. These characteristics, along with biodegradation properties and tissue adhesive behaviour would make any such biomaterial a suitable candidate to address unmet clinical challenges.

Beyond P1, a review article by Ward and Georgiou, entitled "Thermoresponsive Polymers for Biomedical Applications" (*Polymers*, 2011, 3:1215-42) ("P2") may be considered relevant as a teaching of the background art prior to about 2011. This document summarises the properties, chemical structure and applications of different thermoresponsive hydrogels. As noted in P2, the main components and characteristics of some of the more notable hydrogels are summarised in Table 1.

TABLE 1

Prior art as characterised by review document "P2"

| Prior art, as characterised by P2 | | Comparison to |
|---|---|---|
| Material | Characteristics | present invention |
| Butyl methacrylate-poly(N-isopropylacrylamide | Two main components (a) butyl methacrylate and (b) NIPAAm; phase transition behaviour at about 32° C.; and suitable for drug delivery | The five monomeric units of PAS are neither disclosed nor taught by any of the examples provided in P2. Moreover, P2 provides no hint or suggestion that a polymer, when incorporated within a hydrogel carrier may be tuneable. |
| Poly(N-isopropylacrylamide and hydroxyethyl methacrylate | Two components (a) NIPAAm and (b) HEMA; phase transition behaviour at about 32° C.; no control over the mechanical properties; and no study on the degradation behaviour of the polymer | |
| Elastin like polypeptides | One main segment (elastin peptides); lack of mechanical strength; gelation at about 30° C.; and formation of nanoparticles | |
| Poly(N-isopropylacrylamide)-polylactide-dextran | Two components (a) NIPAAm and (b) PLA-dextran; biodegradable; and tunable mechanical properties | This copolymer can form covalent amide bonds with all peptides having free amine groups such as synthetic RGDs. |

Further still, none of the patent literature known to the Applicant at the time of filing appears to disclose, or teach, an antiseptic/analgesic-containing polymer, let alone any commercial forms or medical applications of such a polymer. Representative examples include: U.S. Pat. No. 8,741,317; US 2005/0233003; U.S. Pat. No. 3,290,270; KR 2014093349; CN 201310103994; US 2012/0288564; US 2009/0226519; US 2013/0261212; WO 2014/126537; UA 92027; US 2008/0044476; US 2010/0048473; US 2013/0209532; US 2012/0258068; US 2008/0293827; US 2011/0223230; WO 2001/036000; US 2006/0115457; US 2012/0220691; US 2014/302144; WO 2014/041231; and WO 2014/116187.

Finally, none of the scientific literature known to the Applicant teaches or suggests an antiseptic/analgesic-containing polymer. A representative sample includes: Elvira, et al., *Polymers*, 1997, 38:4743-50; Elvira, et al., *J. Mater. Sci. Mater. Med.*, 2001; 12: 535-42; Zheng, et al., *Biomaterials*, 2004, 25: 1339-48; Park, et al., *Macromol. Symp.*, 2007, 249-250: 145-50; Bessa, et al., *J. Control Release*, 2010, 142:312-8; Chaipinyo, et al., *J. Orthop. Res.*, 2004, 22: 446-55; Nicodemus & Bryant, *J. Biomech.*, 2008, 41: 1528-36; Eastoe, *Biochem J.*, 1955, 61:589-600; Ouimet, et al., *Macromol. Biosci.*, 2015, 15:342-50; and Guan, et al., *Sci. World J.*, 2014, 2014: 1-9.

It is a preferred aim of the present invention to overcome or ameliorate at least one of the disadvantages of the prior art, or to provide a useful alternative.

It is also a preferred aim of a particularly preferred form of the present invention to provide for a polymer for biomedical applications comprising a feasible/sustainable antiseptic moiety. As identified above, known polymers of this type are limited by the burst release of the antiseptic moiety. Accordingly, a preferred form of the present invention seeks to provide a polymer comprising monomeric units "tunable" in their relative proportions so to elicit the following desirous clinical properties: temperature activation, water solubility, mechanical strength, biocompatibility and analgesic/anti-inflammatory properties. The relative proportion of each monomer provides for the "tunability" of the polymer depending upon its specific application. For instance, where a more pronounced antiseptic effect is desired, a greater proportion of the antiseptic moiety is incorporated within the polymer. As described below, preferred embodiments of the inventive polymer may comprise about 5 mol % antiseptic moiety (5-HMA, 4-HMA, or a combination thereof); this amount can be varied depending upon the precise clinical outcome sought.

Although the invention will be described with reference to specific examples it will be appreciated by those skilled in the art that the invention may be embodied in many other forms.

SUMMARY OF THE INVENTION

In a first aspect, provided herein is a polymer comprising at least one antiseptic/analgesic/anti-inflammatory monomeric unit in conjunction with at least three further monomeric units, wherein said three further monomeric units elicit properties selected from the group consisting of: temperature activation, water solubility, mechanical strength, protein/polysaccharide bonding capacity, and combinations thereof.

In a second aspect, provided herein is a method for the synthesis of a polymer as defined according to the first aspect, said method comprising free radical polymerisation of a predetermined molar amount of an initiator; with a predetermined molar amount of an antiseptic/analgesic/anti-inflammatory monomeric unit; with respective predetermined molar amounts of at least three of: a water-soluble monomeric unit; a mechanical strength-conferring monomeric unit; a protein-reactive monomeric unit; and a thermosetting monomeric unit.

In a third aspect, provided herein is use of a polymer as defined according to the first aspect, in medical applications.

In a fourth aspect, provided herein is use of a polymer as defined according to the first aspect, in the treatment of medical conditions comprising cancers.

In a fifth aspect, provided herein is a method of surgical sealing, of dressing a wound, of filling a cavity, or of providing for an in vivo tissue generation scaffold, said method comprising administering to a subject in need of such treatment an effective amount of a polymer as defined according to the first aspect.

In a sixth aspect, provided herein is a method for the treatment of medical conditions comprising cancers, said method comprising administering to a subject in need of such treatment an effective amount of a polymer as defined according to the first aspect. In an embodiment, the cancers comprise lung cancer.

In a seventh, provided herein is a medical kit, said kit comprising: a polymer as defined according to the first aspect; instructions for combining the polymer with a biologically-compatible hydrogel; and optionally a syringe.

DEFINITIONS

With regards to the definitions provided herein, unless stated otherwise, or implicit from context, the defined terms and phrases include the provided meanings. Unless explicitly stated otherwise, or apparent from context, the terms and phrases below do not exclude the meaning that the term or phrase has acquired by a person skilled in the relevant art. The definitions are provided to aid in describing particular embodiments, and are not intended to limit the claimed invention, because the scope of the invention is limited only by the claims. Furthermore, unless otherwise required by context, singular terms shall include pluralities and plural terms shall include the singular.

Throughout the present specification, various aspects and components of the invention can be presented in a range format. The range format is included for convenience and should not be interpreted as an inflexible limitation on the scope of the invention. Accordingly, the description of a range should be considered to have specifically disclosed all the possible sub-ranges as well as individual numerical values within that range, unless specifically indicated. For example, description of a range such as from 1 to 5 should be considered to have specifically disclosed sub-ranges such as from 1 to 3, from 1 to 4, from 1 to 5, from 2 to 4, from 2 to 5, from 3 to 5 etc., as well as individual and partial numbers within the recited range, for example, 1, 2, 3, 4, 5, 5.5 and 6. This applies regardless of the breadth of the disclosed range. Where specific values are required, these will be indicated in the specification.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

For the purposes of interpreting this specification, terms used in the singular will also include the plural and vice versa.

BRIEF DESCRIPTION OF DRAWINGS

A preferred embodiment of the invention will now be described, by way of example only, with reference to the accompanying drawings.

DESCRIPTION OF EMBODIMENTS

Disclosed herein is a class of polymers, based on the poly(N-isopropyl acrylamide-co-N-acryloxysuccinimide-co-2-hydroxyethyl methacrylate/polylactide-co-oligo(ethylene glycol) monomethyl ether methacrylate-co-salicylic acid) polymer, denoted hereinafter as "PAS". The PAS polymer comprises methacrylic ester derivatives of salicylic acid (5-HMA, 4-HMA, or a combination thereof) that display superior analgesic and anti-inflammatory properties by comparison with aspirin.

In addition, the molecular structure of PAS is designed with the intention of addressing the clinical requirements of a biomaterial for tissue regeneration, wound healing and drug delivery. These requirements are, broadly: (a) water solubility; (b) protein/peptide reactivity; (c) a biologically benign crosslinking mechanism; and (d) biodegradability. Thus, the disclosed PAS polymer embodies a blend of such properties, tunable depending upon the precise clinical application to which it is extended.

In order to enhance water-solubility characteristics, PAS incorporates a hydrophilic ethylene glycol (OEGMA) segment in its molecular structure. The PAS polymer can also bond with proteins in aqueous solution due to an N-acryloxysuccinimide (NAS) segment. The presence of a thermally-responsive fraction in the form of N-isopropyl acrylamide (NIPAAm) can induce hydrogel formation at body temperature without the need for the addition of any external chemical(s)/reagent(s). Moreover, the PAS polymer is bioresorbable upon the cleavage of polylactide-co-2-hydroxyethylmethyl acrylate (PLA/HEMA) from the polymer. Finally, an analgesic/antiseptic moiety is provided in the form of methacrylic ester derivatives of salicylic acid (5-HMA, 4-HMA, or a combination thereof). The molecular structure of the PAS polymer and the role of each segment are shown schematically in FIG. 1. It will be appreciated that the relative proportions of each monomeric unit provides for the purported tunability of the PAS polymer depending upon the clinical application to which the PAS polymer will be applied.

The Applicant has unexpectedly found that PAS polymer, when incorporated within a hydrogel carrier, has physicochemical properties that may be tuned to one or more specific clinical needs (e.g., temperature responsiveness, biocompatibility, mechanical properties, etc.). In particular, the PAS polymer comprises methacrylic ester derivatives of salicylic acid (5-HMA, 4-HMA, or a combination thereof) which is shown to display outstanding analgesic and anti-inflammatory properties.

Accordingly, disclosed herein is the synthesis of poly(N-isopropyl acrylamide-co-N-acryloxysuccinimide-co-2-hydroxyethyl methacrylate/polylactide-co-oligo(ethylene glycol) monomethyl ether methacrylate-co-salicylic acid), denoted hereinafter as PAS. This polymer has the potential to address many of the current shortfalls associated with known materials, such as chronic inflammation, low host tissue adhesivity, low biological activity, and cytotoxic crosslinking mechanism.

In its broadest form, the present disclosure relates to the PAS polymer, per se. The PAS polymer comprises monomeric units tunable in their relative proportions so to elicit the following desirous clinical properties: temperature activation, water solubility, mechanical strength, biocompatibility and analgesic/anti-inflammatory properties; the relative proportion of each monomer provides for the tunability of the PAS polymer depending upon its specific application.

In a first aspect, provided herein is a polymer comprising at least one antiseptic/analgesic/anti-inflammatory monomeric unit in conjunction with at least three further monomeric units, wherein said three further monomeric units elicit properties selected from the group consisting of: temperature activation, water solubility, mechanical strength, protein/polysaccharide bonding capacity, and combinations thereof.

In an embodiment, the antiseptic/analgesic/anti-inflammatory monomeric unit comprises a methacrylic ester derivative of salicylic acid (5-HMA or 4-HMA, or a combination thereof).

In one embodiment the polymer comprises, in approximate relative molar proportions, 5-HMA or 4-HMA, or a combination thereof, in an amount in a range of about 2 mol % to about 10 mol %, for example: about 2 mol %, about 3 mol %, about 4 mol %, about 5 mol %, about 6 mol %, about 7 mol %, about 8 mol %, about 9 mol %, or about 10 mol %.

In an embodiment, the at least three further monomeric units are selected from the group consisting of: a water-soluble monomeric unit in the form of a hydrophilic ethylene glycol (OEGMA) moiety; a mechanical strength-conferring monomeric unit in the form of polylactide-co-2-hydroxy-ethylmethyl acrylate (PLA/HEMA); a protein/polysaccharide-reactive monomeric unit in the form of an N-acryloxysuccinimide (NAS) moiety; and a thermosetting monomeric unit in the form of an N-isopropyl acrylamide (NIPAAm) moiety.

In an embodiment, the relative proportions of each of said at least three monomeric units provides for the resultant polymer to be tuned/optimised for a defined clinical application, in which certain physical/chemical/biological properties are preferred over others.

In an embodiment, the defined antiseptic/analgesic/anti-inflammatory properties are preferred in applications in which chronic inflammation may lead to clinical complications.

In an embodiment, the water-soluble monomeric unit, in the form of a hydrophilic ethylene glycol (OEGMA) moiety, provides for defined water solubility, thereby to substantially avoid the use of organic solvents in preparation of the polymer.

In an embodiment, the water-soluble monomeric unit, in the form of a hydrophilic ethylene glycol (OEGMA) moiety, provides for a controllable gelation time, to in turn provide for relatively fast gelation for superficial zones/surgical sealants and/or relatively slow gelation for deep tissue regeneration. Herein "fast gelation" is regarded as the formation of a gel in less than 1 minute at 37° C. In one embodiment hydrophilic ethylene glycol (OEGMA) moiety, provides for a fast gelation time.

In an embodiment, the mechanical strength conferring monomeric unit provides controllable mechanical strength, flexibility and elasticity to tune the polymer to the specific requirements of a given application.

In an embodiment, the mechanical strength conferring monomeric unit provides tissue adhesive behaviour to the polymer, thereby to facilitate retention of a deposit of said polymer at a delivery site.

In an embodiment, the mechanical strength-conferring monomeric unit, in the form of polylactide-co-2-hydroxy-ethylmethyl acrylate (PLA/HEMA), provides for: degradation properties, wherein the hydrogel is bioresorbable through the kidney upon the gradual cleavage of PLA; and tissue adhesivity, to prevent the displacement and leakage of the hydrogel to the surrounding tissues. The length of the PLA units can be tailored for the applications. In one embodiment the PLA/HEMA unit comprises 1, 2, 3, 4, 5, 6, 7, 8, 9 or 10 PLA units. For example the PLA/HEMA unit may comprise 5 PLA units.

In an embodiment, the amount of water-soluble monomeric unit and the mechanical strength conferring monomeric unit provide controllable bioresorption behaviour.

In an embodiment, the protein-reactive monomeric unit, in the form of an N-acryloxysuccinimide (NAS) moiety, provides for: peptide reactivity by way of bonding different biologically-active peptides and polysaccharides to the hydrogel to promote cell signalling and tissue formation rate.

In one embodiment the polymer comprises, in approximate relative molar proportions, NAS, in an amount in a range of about 10 mol % to about 15 mol %, for example about 10 mol %, about 11 mol %, about 12 mol %, about 13 mol %, about 14 mol %, or about 15 mol %.

In an embodiment, the thermosetting monomeric unit, in the form of an N-isopropyl acrylamide (NIPAAm) moiety, provides for: thermosetting properties by way of inducing the structure formation in situ at about 37° C.

In another embodiment, the polymer comprises, in approximate relative molar proportions, NIPAAm, in an amount in a range of about 60 mol % to about 80 mol %, for example in a range of about 60 mol % to about 70 mol %, or a range of about 70 mol % to about 80 mol %. Exemplary values include about 68 mol %, or about 75 mol %.

In an embodiment, the polymer is dissolved in an aqueous solution with the mass content of 10 mg/mL to 700 mg/mL at 0-35° C., for example the mass content may be in a range of 35 mg/mL to 400 mg/mL at 0-35° C.

In an embodiment, the polymer forms a micro- or macro-structures in situ by increasing the temperature to 37° C. or higher.

In an embodiment, the biological efficacy of the polymer is confirmable by way of cytocompatibility and microbial colony counting studies.

In one embodiment the polymer has a compressive Modulus in a range of about 200 kPa to about 400 kPa. For example the compressive Modulus may be: about 200 kPa, about 220 kPa, about 240 kPa, about 260 kPa, about 280 kPa, about 300 kPa, about 320 kPa, about 340 kPa, about 360 kPa, about 380 kPa, or about 400 kPa.

In another embodiment the polymer may have a tensile modulus in a range of about 500 kPa to about 800 kPa. For example the tensile modulus may be: about 500 kPa, about 520 kPa, about 540 kPa, about 560 kPa, about 580 kPa, about 600 kPa, about 620 kPa, about 640 kPa, about 660 kPa, about 680 kPa, about 700 kPa, about 720 kPa, about 740 kPa, about 760 kPa, about 780 kPa, or about 800 kPa.

In an embodiment, the mechanical properties of the polymer hydrogel, by way of compressive and tensile strengths are about 311±47 kPa and about 781±116 kPa, respectively.

In another embodiment the polymer may have an adhesion shear strength in a range of about 900 kPa to about 1200 kPa. Alternatively, the adhesion shear strength may be: at least about 900 kPa, at least about 920 kPa, at least about 940 kPa, at least about 960 kPa, at least about 980 kPa, at least about 1000 kPa, at least about 1020 kPa, at least about 1040 kPa, at least about 1060 kPa, at least about 1080 kPa, at least about 1100 kPa, at least about 1120 kPa, at least about 1140 kPa, at least about 1160 kPa, at least about 1180 kPa, or at least about 1200 kPa.

In an embodiment, in tissue adhesion tests of the polymer may have an adhesion shear strength of at least about 970 kPa.

Figure 1:
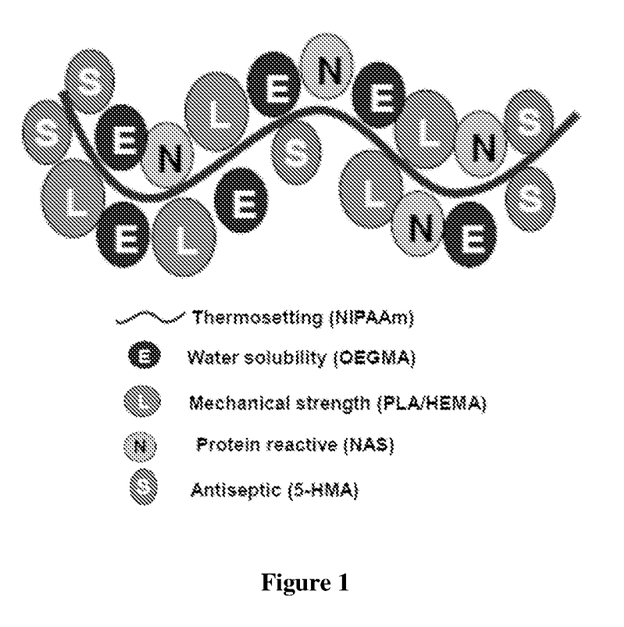
FIG. 1 is a schematic representation of the PAS polymer of the present invention. The thermosetting monomer is represented as the NIPAAm backbone; the water-soluble OEGMA monomer is designated "E"; the mechanical strength conferring PLA/HEMA monomer is designated "L"; the protein-reactive NAS monomer is designated "N"; and the antiseptic 5-HMA monomer is designated "S". As noted elsewhere, the 5-HMA moiety is readily interchangeable or combinable with 4-HMA. The number of each said monomer in the drawing represents its relative proportion.

In an embodiment, the polymer is represented, schematically, by the structure provided in FIG. 1 of the accompanying drawings.

In an embodiment, the polymer is clinically useful. For example the polymer may be used as: a surgical sealant, wound healing dressing, filler and/or an in vivo tissue regeneration scaffold.

In an embodiment, the polymer comprises, in approximate relative molar proportions, less than about 5 mol % OEGMA, thereby to elicit water-solubility. In another embodiment, the polymer comprises, in approximate relative molar proportions, OEGMA in a range of about 2 mol % to about 5 mol %, for example about 2 mol %, about 3 mol %, about 4 mol % or about 5 mol %.

In an embodiment, the polymer comprises, in approximate relative molar proportions, PLA/HEMA in a range of about 2 mol % to about 10 mol %. For example the PLA may be present in an amount of: about 2 mol % PLA/HEMA, about 3 mol % PLA/HEMA, about 4 mol % PLA/HEMA, about 5 mol % PLA/HEMA, about 6 mol % PLA/HEMA, about 7 mol % PLA/HEMA, about 8 mol % PLA/HEMA, about 9 mol % PLA/HEMA, or about 10 mol % PLA/HEMA In an embodiment, the polymer comprises, in approximate relative molar proportions, greater than about 8 mol % PLA/HEMA. In particular, in an embodiment the polymer comprises, in approximate relative molar proportions, greater than about 8 mol % PLA/HEMA in an embodiment thereby to elicit hydrogel formation at about 37° C. For example, the polymer may comprise greater than about 8 mol % PLA/HEMA, greater than about 9 mol % PLA/HEMA, greater than about 10 mol % PLA/HEMA, greater than about 11 mol % PLA/HEMA, greater than about 12 mol % PLA/HEMA, greater than about 13 mol % PLA/HEMA, greater than about 14 mol % PLA/HEMA, or greater than about 15 mol % PLA/HEMA.

In an embodiment, the polymer comprises, in approximate relative molar proportions, NIPAAm (68 mol %), NAS (14 mol %), PLA/HEMA (8 mol %), OEGMA (5 mol %) and 5-HMA (5 mol %). In another embodiment, 4-HMA (5 mol %) was applied as the antiseptic moiety. In another embodiment, a combination of 5-HMA (2.5 mol %) and 4-HMA (2.5 mol %) was applied as the antiseptic moiety. Amongst other properties, the polymer of these embodiments is water-soluble and forms a hydrogel at about 37° C.; it also elicits desirous antibacterial/antiseptic properties by way of the 5-HMA (or 4-HMA, or a combination thereof) component.

In an embodiment, the polymer provides for relatively safe and effective in vivo delivery of said polymer to a surgical site without clinical complications by way of foreign body immune responses and chronic inflammation in a subject.

In an embodiment, the polymer provides a vehicle to prevent burst release of the antiseptic/analgesic/anti-inflammatory effects from the methacrylic ester derivatives of salicylic acid, over period of about 0 days to about 270 days or thereby reducing the time-based incidence of infection at a surgical site.

In an embodiment, the period of about 0 to about 270 days is preferably about 10 to about 260 days; more preferably about 20 to about 250 days; more preferably still about 30 to about 240 days; more preferably still about 40 to about 230 days; more preferably still about 50 to about 220 days; more preferably still about 60 to about 210 days; more preferably still about 70 to about 200 days; more preferably still about 80 to about 190 days; more preferably still about 90 to about 180 days; more preferably still about 100 to about 170 days; more preferably still about 110 to about 160 days; more preferably still about 110 to about 150 days; more preferably still about 120 to about 140 days; and more preferably still about 130 days.

Within the defined period of about 0 to about 270 days is included: 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269 and 270 days, as well as part days.

In an embodiment, the polymer bonds with natural and synthetic peptides or polysaccharides.

In an embodiment, the polymer further comprises, or is compatible with one or more cells to assist in the repair of biological tissue. The cells may be regenerative cells, including but not limited to: fibroblast, endothelial cells, progenitor cells, or mixtures thereof.

In an embodiment, the one or more cells are distributed relatively evenly throughout the polymer.

In an embodiment, the number of the one or more cells in the polymer is between about $10^2$ and about $10^8$ cells/mL. In another embodiment, the number of the one or more cells in the polymer is between about $10^3$ and about $10^5$ cells/mL.

In a second aspect, provided herein is a method for the synthesis of a polymer as defined according to the first aspect, said method comprising free radical polymerisation of a predetermined molar amount of an initiator; with a predetermined molar amount of an antiseptic/analgesic/anti-inflammatory monomeric unit; with respective predetermined molar amounts of at least three of: a water-soluble monomeric unit; a mechanical strength-conferring monomeric unit; a protein-reactive monomeric unit; and a thermosetting monomeric unit.

In an embodiment, the method further comprises an extraction step wherein the polymer is precipitated in water at about 32° C. to remove unreacted monomers, and filtered, thereby to provide a crude PAS polymer.

In an embodiment, the method further comprises a purification step wherein the precipitated polymer is dissolved in ethanol and re-precipitated in water at about 32° C., thereby to provide a purified PAS polymer.

In an embodiment, the polymer is dried under reduced pressure for a period of about 48 hours at a temperature of about 40° C. prior to use.

In an embodiment, the antiseptic/analgesic/anti-inflammatory monomeric unit is 5-HMA, 4-HMA, or a combination thereof; and if present, the water-soluble monomeric unit is NIPAAm; the mechanical strength-conferring monomeric unit is NAS; the protein-reactive monomeric unit is PLA/HEMA; and the thermosetting monomeric unit is OEGMA.

In an embodiment, the predetermined molar amount of 5-HMA, 4-HMA, or a combination thereof is about 5 mol %; and if present, the predetermined molar amount of NIPAAm is about 68 mol %; the predetermined molar amount of NAS is about 14 mol %; the predetermined molar amount of PLA/HEMA is about 8 mol %; and the predetermined molar amount of OEGMA is about 5 mol %. The skilled person will recognise this as a representative embodiment only; the relative proportions may be changed depending upon the clinical need.

In a third aspect, provided herein is use of a polymer as defined according to the first aspect, in medical applications. In one embodiment, the medical applications may include use as a surgical sealant, a wound healing dressing, a filler, or the polymer may be utilised for in vivo tissue regeneration and/or in vitro cell growth scaffolding.

In a fourth aspect, provided herein is use of a polymer as defined according to the first aspect, in the treatment of medical conditions comprising cancers. In an embodiment, the cancers comprise lung cancer, however it would be appreciated that the polymer disclosed herein has surgical sealant properties and may be amenable with any tumour removal procedure that is prone to bleeding.

In a fifth aspect, provided herein is a method of surgical sealing, of dressing a wound, of filling a cavity, or of providing for an in vivo tissue generation scaffold, said method comprising administering to a subject in need of such treatment an effective amount of a polymer as defined according to the first aspect.

In a sixth aspect, provided herein is a method for the treatment of medical conditions comprising cancers, said method comprising administering to a subject in need of such treatment an effective amount of a polymer as defined according to the first aspect. In an embodiment, the cancers comprise lung cancer.

Furthermore, in a seventh, provided herein is a medical kit, said kit comprising: a polymer as defined according to the first aspect; instructions for combining the polymer with a biologically-compatible hydrogel; and optionally a syringe.

Each of the aspects of the invention as identified herein, is linked by the special technical feature of the PAS polymer, per se. Thus, the invention resides in the PAS polymer, commercial forms and uses thereof.

On the basis of the prior art information known to the Applicant at the time of filing, novelty resides in a polymer comprising the specific combination of monomeric units defined by PAS.

Further novel aspects of the invention could include: methods for the synthesis of PAS (generic and specific "tuned" forms); use of PAS in medical applications (e.g., lung cancer); methods of medical treatment (e.g., lung cancer) using PAS; a medical kit comprising PAS and a compatible hydrogel (and optionally a syringe); and PAS when incorporated within a hydrogel carrier (i.e., PASGel).

EXAMPLES

The PAS polymer was sought due to the Applicant having identified deficiencies in the art, such as chronic inflammation, low host tissue adhesivity, low biological activity, and a cytotoxic crosslinking mechanism. The PAS polymer comprises methacrylic ester derivatives of salicylic acid (5-HMA, 4-HMA, or a combination thereof) which itself displays analgesic and anti-inflammatory properties. PAS is water-soluble due to the presence of a hydrophilic ethylene glycol (OEGMA) segment. This polymer also can bond with proteins in aqueous solution through its N-acryloxysuccinimide (NAS) segment. The presence of a thermally-responsive fraction (N-isopropyl acrylamide, NIPAAm) induces hydrogel formation at body temperature without the need for the addition of further reagents. Finally, the PAS polymer is bioresorbable upon the cleavage of polylactide-co-2-hydroxy-ethylmethyl acrylate (PLA/HEMA) from the polymer.

Figure 2:
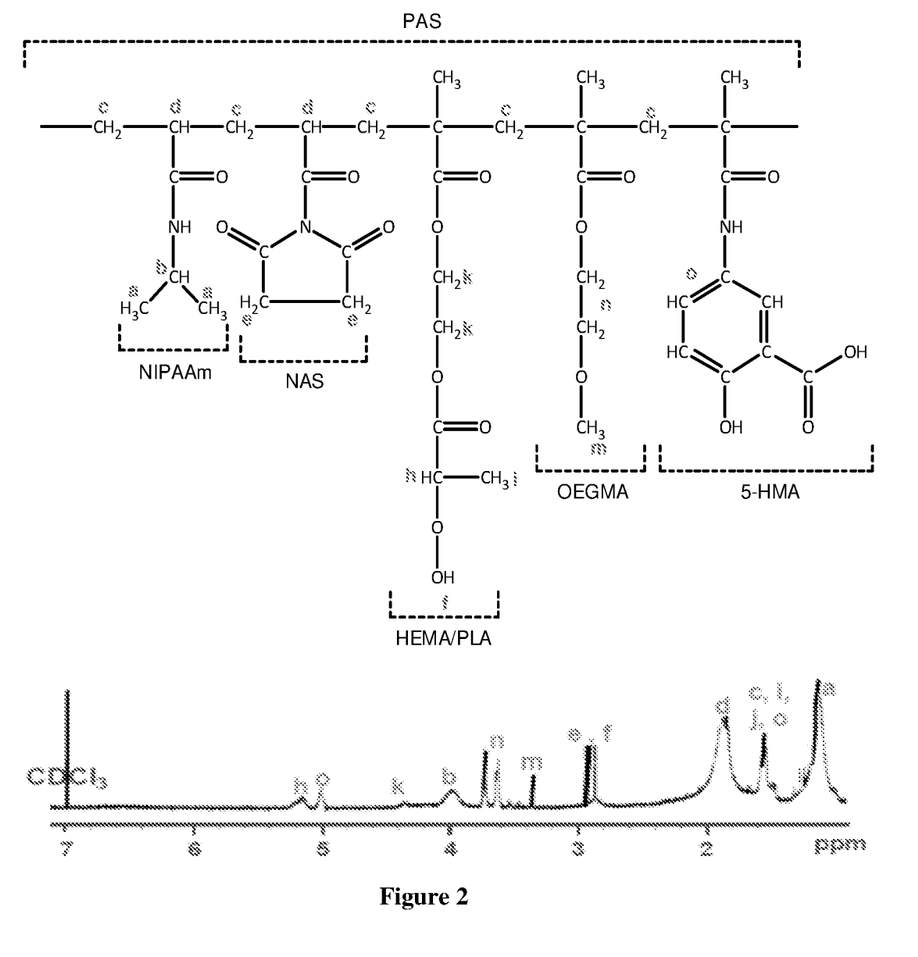
FIG. 2 is a $^1$H NMR spectrum of the PAS polymer, with the respective resonances assigned as indicated. The spectrum readily confirms the incorporation of all five monomeric units within the polymer, with the antiseptic 5-HMA protons designated "o" appearing, in accordance with expectation, at about 1.5 ppm.

The presence of all five monomeric units within the inventive polymer is readily confirmed by $^1$H NMR (FIG. 2).

Figure 3:
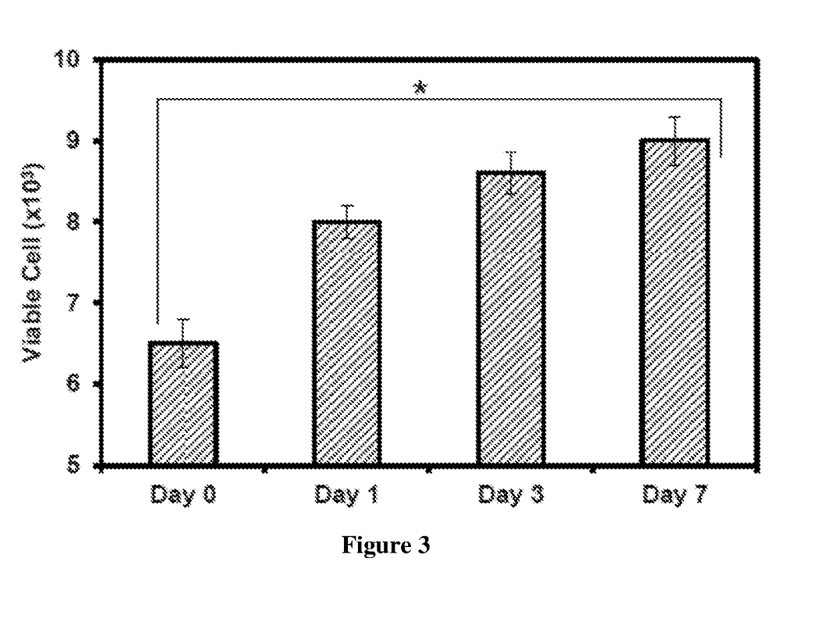
FIG. 3 shows the biological efficacy of PAS when incorporated within a hydrogel carrier (PAS Gel). The results of a preliminary cytocompatibility study is shown in which the viable cell count increased from about $6.5 \times 10^3$ on day "0" to about $9 \times 10^3$ on day "7"; an approximate 50% increase over a one week period.
Figure 4:
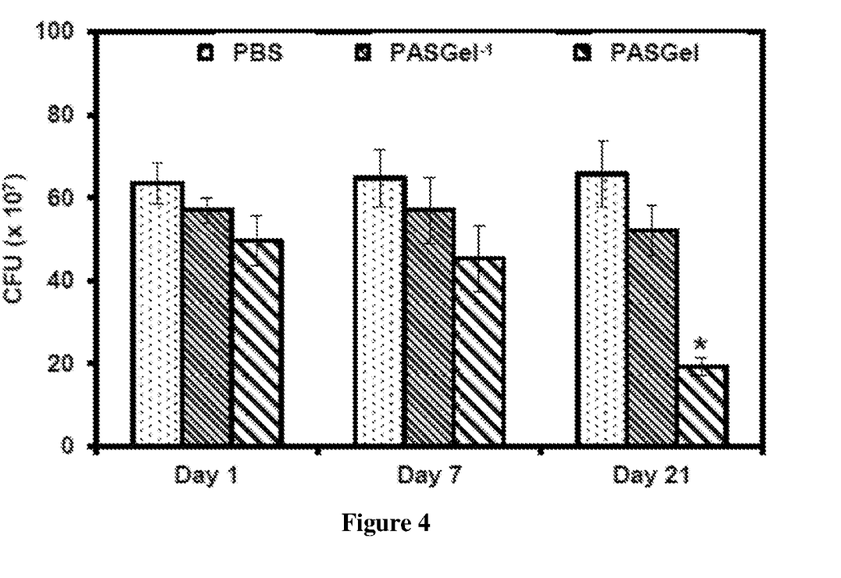
FIG. 4 also shows the biological efficacy of PAS when incorporated within a hydrogel carrier (PAS Gel). The results of a preliminary microbial colony counting study is shown in which the PASGel sample at day "21" supported only about $2 \times 10^8$ CFU; this is about one third of the original (day "1") count.
Figure 5:
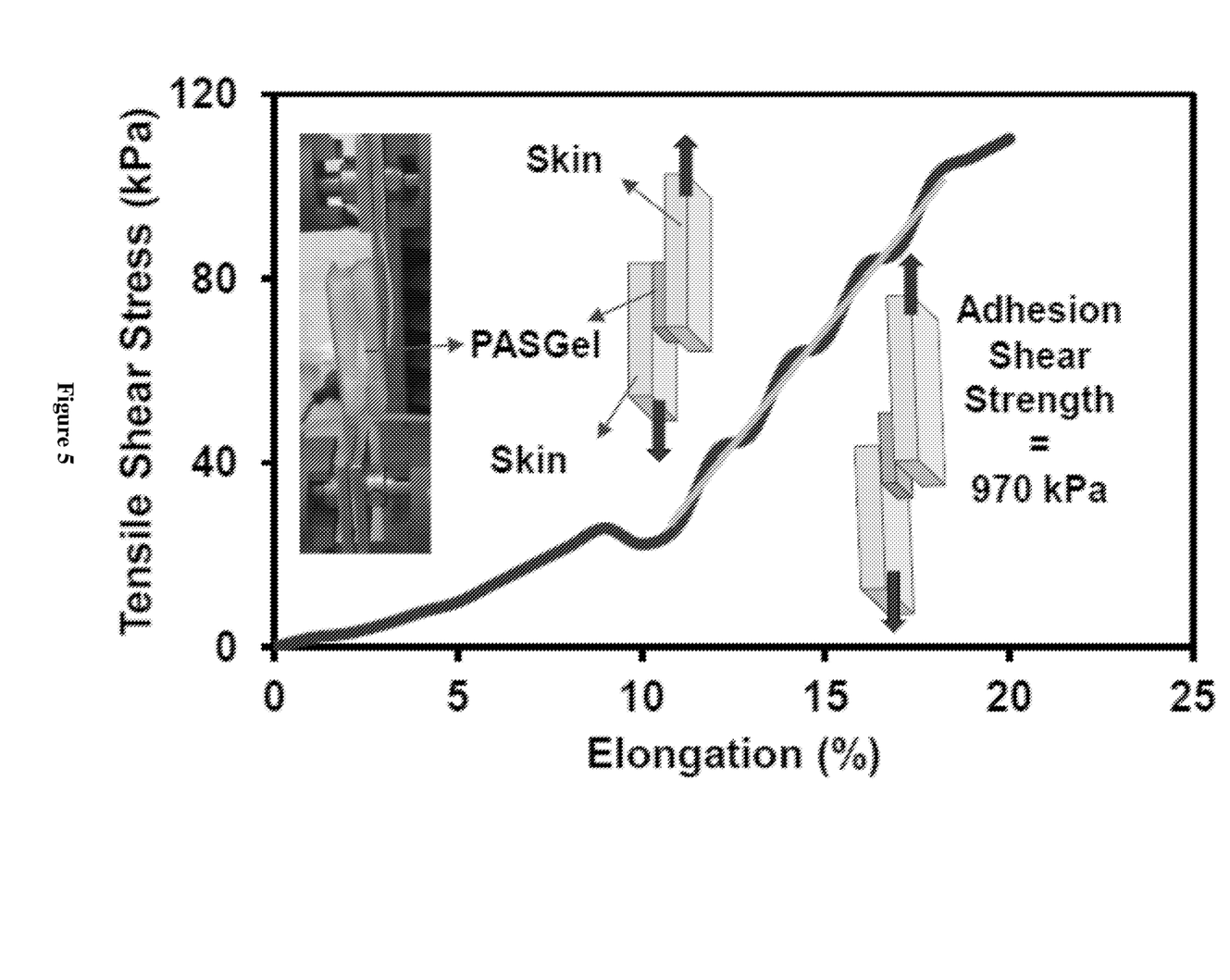
FIG. 5 shows that the PASGel gives rise to advantageous mechanical properties by way of the compressive and tensile strengths (311±47 kPa and 781±116 kPa, respectively), as well as tissue adhesion tests (970 kPa).

The biological and physical profiles of the PAS polymer can be readily demonstrated. For instance, the biological efficacy of PAS when incorporated within a hydrogel carrier ("PASGel") has been shown by preliminary cytocompatibility and microbial colony counting studies (FIG. 3 and FIG. 4, respectively). Further, advantageous mechanical properties were apparent from analysing the compressive and tensile strengths of the PAS polymer (311±47 kPa and 781±116 kPa, respectively), as well as tissue adhesion tests (FIG. 5).

TABLE 2

Form and function of each monomeric unit of the inventive PAS polymer

| Monomer | Role/s | Significance |
|---|---|---|
| 5-HMA, 4-HMA or combination | Anti-inflammatory, antiseptic and anti-microbial properties | Suppresses chronic inflammation as this inflammation may lead to severe clinical complications |
| OEGMA | Water solubility | Prevents the use of organic solvents in the preparation of hydrogel to enhance the biological properties of the biomaterial |
|  | Controllable gelation time | Addresses clinical needs which are present for different applications, fast gelation for superficial zones/surgical sealants and slow gelation for deep tissue regeneration |
| NAS | Peptide reactivity | Bonds different biologically active peptides to PASGel to promote cell signalling and tissue formation rate, |
| NIPAAm | Thermosetting properties | Preferably induces hydrogel formation in situ at 37° C.; this prevents the use of toxic crosslinking reagents |
|  | Injectability | Delivers the hydrogel to different parts of the body in a minimally-invasive manner |
| HEMA/PLA | Degradation | Make PASGel bioresorbable through kidney upon the gradual cleavage of PLA |
|  | Tissue adhesion | Prevent displacement and leakage of the hydrogel to the surrounding tissues |

Preferred forms of the PAS polymer, per se, may reside in PAS synthesised with a feed of NIPAAm (68 mol %), NAS (14 mol %), PLA/HEMA (8 mol %), OEGMA (5 mol %) and 5-HMA/4-HMA (5 mol %), in the presence of an initiator such as 4,4'-azobis-4-cyanovaleric acid; this composition is found to be water-soluble and formed a hydrogel at 37° C.

An immediate distinction over the known prior art is that although salicylic acid has previously been chemically bonded with different monomers, e.g., 3,5-di(acrylyloxymethyl)-salicylic acid; 3-methyl-S-acryloxymethyl salicylic acid (see, e.g., U.S. Pat. No. 3,290,270), this is the first time that a class of injectable salicylic acid based thermosetting hydrogels have been designed with the capacity to bond with natural and synthetic peptides. These characteristics, along with the biodegradation properties and tissue adhesive behaviour of PASGel make this biomaterial a suitable candidate to address presently unmet clinical challenges.

The Applicant has confirmed the formation of PAS polymer by using $^1$H NMR analysis. In addition, in vitro studies showed the gradual release of salicylic acid and its biological activity. Also, the Applicant has confirmed the cytocompatibility of PAS Gel with fibroblasts cells in vitro. The physical characterisation experiments also confirmed suitable mechanical performance of the developed material for wound healing and tissue engineering.

In vivo cytocompatibility study with mice subcutaneous models is required and will be conducted in the short term. More complex animal models, e.g., sheep lung bleeding, will also be carried out to ensure the efficacy of this technology.

PAS Polymer Synthesis and Molecular Characterisation

Synthesis of the PAS polymer gave rise to several unexpected challenges, each of which was addressed in an inventive manner by the Applicant. For instance, during purification of 5-HMA monomer, recrystallization of this monomer by using water and methanol required a specific volume ratio of the two solvents (0.5:2, water:methanol), to ensure complete dissolution and recrystallization of the product.

Secondly, the during synthesis of the PAS polymer, the molar ratio of the initiator (4,4'-azobis-4-cyanovaleric acid) was changed in the feed solution to assure suitable degree of polymerisation of PAS polymer. Lastly, during the synthesis of the PAS polymer, five different monomers were used, each presenting unique challenges by way of their mutual compatibility.

The feed amounts of the five monomers were tuned to, on one occasion, synthesise a water-soluble polymer. The Applicant found that polymers synthesised with less than 5 mol % OEGMA, were not water-soluble. Also, PAS polymers with above 8 mol % OEGMA were not converted to hydrogel at 37° C. Therefore, these formulations of PAS polymer were not suitable for the fabrication of injectable biomaterials. By testing multiple formulations, it was found empirically that PAS synthesised with feed of NIPAAm (68 mol %), NAS (14 mol %), PLA/HEMA (8 mol %), OEGMA (5 mol %) and 5-HMA/4-HMA (5 mol %) was water-soluble and formed hydrogel at 37° C. Further studies are required to alter the composition of PAS polymer to tune the physicochemical properties of PASGel for different biomedical applications.

For the synthesis of PAS, commercially available monomers, e.g., NIPAAm, NAS and OEGMA and in-house pre-synthesised monomers, PLA/HEMA and 5-HMA were used. The synthesis method of PLA/HEMA was developed by Dijk-Wolthuls, et al., [Tsanga, Boschb and Dijk-Wolthuls; "A new class of polymerisable dextrans with hydrolysable groups: hydroxyethyl methacrylated dextran with and without oligolactate spacer", Polymer, 38, 6235-6242, 1997] and was previously optimised for the formation of PLA/HEMA with six lactate lengths per HEMA molecule [Fathi, Mithieux, Wei, Chrzanowski, Valtchev and Weiss; "Elastin based cell-laden injectable hydrogels with tunable gelation, mechanical and biodegradation properties", Biomaterials 35(21), 5425-5435, 2014].

Synthesis of the 5-HMA (Antiseptic) Monomer

The synthetic method for the preparation of 5-HMA, one of the monomers used in the synthesis of PAS polymer, is adapted from that prescribed by San Roman, et al. [an initial study is shown in Elvira and San Roman, "Synthesis and stereochemistry of isomeric methacrylic polymers derived from 4- and 5-aminosalicylic acids", Polymer, 38, 4743-4750, 1997; and a follow-up study is disclosed in Elvira, Gallardo, Lacroix, Schacht, San Roman, "Incorporation of salicylic acid derivatives to hydrophilic copolymer systems with biomedical applications", *J Mater Sci Mater Med,* 12, 535-542, 2001].

Briefly, the method of synthesis of the 5-HMA monomer is initially outlined in the Elvira and San Roman citation. Then throughout the follow-up study, this monomer was polymerised with 2-hydoxyethyl methacrylate (HEMA). In the inventive synthesis of PAS polymer, the Applicant bonded 5-HMA with oligo(ethylene glycol) (OEGMA), N-acryloxy succinimide ester (NAS), N-isopropylacrylamide (NIPAAm), and polylactide (HEMA/PLA). Each and every segment of the resulting molecule has a vital role to address different clinical requirements for tissue regeneration, drug delivery and to use PASGel as a surgical sealant. The functions of these various monomers in the synthesis of PASGel are summarised in Table 2.

5-HMA was synthesised by selective amidation of 2-amino-5-hydroxybenzoic acid with methacrylolyl chloride. To this end, 50% v/v methacrylolyl chloride solution in tetrahydrofuran (THF) was added, with the flow rate of 0.5 mL/min to 10% w/w 2-amino-5-hydroxybenzoic acid solution in THF. The resulting solution was stirred at 300 rpm and 4° C. under a nitrogen blanket, equipped with a condenser, for 6 hours. The resulting functionalised monomer suspension was filtered to remove suspended by-product salts.

The resulting clear solution was dried with a rotary evaporator at 40° C. under reduced pressure, resulted in the formation of a viscous brown paste. The 5-HMA monomer paste was then dissolved in water/methanol solution (4:1 volume ratio) and recrystallised with water/methanol solution (1:2 volume ratio) at 4° C. to remove unreacted 2-amino-5-hydroxybenzoic acid and methacrylolyl chloride. The beige crystallised monomers were separated by filtration and the recrystallization process, as described above using water/methanol, was repeated three times to acquire highly purified 5-HMA monomer.

As disclosed herein, 4-HMA can be used instead of, or in combination with 5-HMA; the antiseptic effect is largely the same, as shown in C. Elvira et al., *Polymer,* 38(18), 4743-4750, 1997.

Synthesis of the PAS Polymer

The PAS polymer was synthesised by free radical polymerisation of NIPAAm (68 mol %), NAS (14 mol %), PLA/HEMA (8 mol %), OEGMA (5 mol %) and 5-HMA (5 mol %) in THF at 70° C. by using 0.3 mol % 4,4'-azobis (4-cyanovaleric acid) as an initiator. After 24 hours, the resulting polymer solution was precipitated in water at 32° C. to remove unreacted monomers. The precipitated polymer was then dissolved in ethanol and re-precipitated in water under the same conditions. The resulting polymer was then dried under reduced pressure at 40° C. for 48 hours.

In FIG. 2, the presence of corresponding bonds for all five primary segments of PAS confirmed the successful synthesis of the polymer. A variety of PAS polymers can be synthesised by using different amounts of feed monomers. Thus, the exemplified NIPAAm (68 mol %), NAS (14 mol %), PLA/HEMA (8 mol %), OEGMA (5 mol %) and 5-HMA (5 mol %) polymer is representative only. In particular, 4-HMA (5 mol %) or a combination of 5-HMA (e.g., 2.5 mol %) and 4-HMA (e.g., 2.5 mol %) can be applied as the antiseptic moiety.

Peptide Hydrogel Formation and Cytocompatibility

The synthesised PAS polymer with 5 mol % OEGMA content was found to be water-soluble. To confirm the peptide-reactivity of the polymer, GRGDS ({GLY}{ARG}{GLY}{ASP}{SER}) synthetic peptide was used as a model peptide. GRGDS mimics the cellular binding site of many adhesive proteins in the extracellular matrix and causes rounding and detachment of spread cells. The GRGDS peptide has intermediate affinity to V3 and IIb3, which are the integrins most reported to be involved in bone function. PAS (150 mg/mL) and GRGDS (1 mg/mL) were mixed and allowed to react for 8 hours at 4° C. The resulting PAS-co-GRGDS (PASGel) solution was then converted to hydrogel with the increase of temperature to physiological temperature (e.g., 37° C.).

To test the cytocompatible properties of PASGel, fibroblast cells (GM3348) were encapsulated within the structure of the PASGel hydrogels for up to 7 days. The results in FIG. 3 confirmed the cytocompatibility of the hydrogels as the number of viable cells was continuously increased for at least seven days post-culture.

The unique biomolecular structure of PASGel allows the controlled dual-delivery of (a) biologically active peptides to induce tissue-specific cell signalling and (b) salicylic acid with proved anti-inflammatory and anti-bacterial properties. GRGDS peptide was chemically bonded to the molecular structure PASGel. A Bradford protein assay was used to confirm the formation of covalent bonds between PAS polymer and peptides. To this end, immediately after post-hydrogel formation, PASGels were washed thoroughly three times with warm phosphate buffered saline (PBS) to leach out unreacted GRGDS from the structure PASGel. The concentration of the peptide in the washing media was measured by the Bradford protein assay to calculate the amount of covalently-bonded GRGDS in PASGels. These results showed that nearly 94% of the GRGDS was covalently bonded to the structure of PASGel. The capacity of the PASGel to deliver and over time release of biologically active salicylic acid was also studied.

The formation of chemical bonds allows controlled delivery of bioactive compounds in vivo but it may destructively affect the biological activity of the compound. The activity of the incorporated salicylic acid is, therefore, of critical importance. To this end, the Applicant assessed the antimicrobial properties of the incorporated 5-HMA/4-HMA as an indication to confirm gradual release of bioactive salicylic acid from PASGel.

The Applicant compared the anti-microbial properties of PASGel with PASGel$^{neg}$ (i.e., without incorporated salicylic acid in PAS polymer) by slightly modifying the standard test method under dynamic contact conditions (ASTME 2149). Briefly, PAS Gel and PASGel$^{neg}$ hydrogels were prepared under aseptic conditions and incubated in filter-sterilised PBS for 21 days. Preliminary results showed that the overall degradation rates of PASGel and PASGel$^{neg}$ within this period are nearly 30 wt %. The samples from the incubation media at different time points, e.g., after 1 day, 7 and 21 days, were used to analyse the antimicrobial properties of these hydrogel over time.

Three *E. coli* colonies were harvested with inoculation loops and then added to 3 mL of the soaking solutions of PASGel and PASGel$^{neg}$ at days 1, 7 and 21. Filter-sterilised PBS was also used to grow three colonies as the control. The microbial suspensions were then incubated at 37° C. for 5 hours. Serial dilutions were performed, and the diluted bacterial suspensions of $10^{-6}$ and $10^{-7}$ were inoculated to nutrient agar plates for 16 hours and then the numbers of colonies were counted to calculate colony forming units (CFU).

The microbial colony counting results in FIG. 4 showed that there is no significant difference among the control group and the washing media of PASGel and PASGel$^{neg}$ samples after 1 day and 7 days of soaking. However, the results from day 21 confirmed a three-fold decrease in the number of colonies for PASGel compared with PASGel$^{neg}$ samples and PBS control. These results confirmed the biological activity of the cleaved salicylic acid from the structure of PASGel hydrogel. In addition, the release of salicylic acid over time showed the chemical bonding of this compound within the structure of PASGel hydrogel.

Tissue Adhesion

In tissue engineering, drug delivery and wound dressing applications, tissue adhesiveness of the biomaterials is of great importance to prevent clinical complications such as tissue leakage. To assess this characteristic of PASGel, the Applicant used the ex vivo ASTMD3164-03 (2014) standard method with pig skin. For this analysis, 100 μL of PASGel was used to fill a 0.5×0.5 cm$^2$ area to glue two pieces of pig skin together.

The elongation force to move apart these two pieces of skin was measured with Instron 5943 and it reaches plateau at 7.5 N. The results in FIG. 5 showed that the shear stress on PASGel was nearly 1 MPa. These results showed high tissue adhesive properties of the PASGel.

Physical Characterisation

At simulated physiological conditions, the PASGel hydrogel displayed respectively, the compression and tensile moduli of 311±47 kPa and 781±116 kPa. These mechanical performance parameters are paramount compared with previously developed or commercially available hydrogels. For instance, Neocart hydrogel that is in a clinical trial phase for cartilage repair possesses the compression modulus less than 10 kPa [Ahmed and Hincke, "Strategies for articular cartilage lesion repair and functional restoration" *Tissue Eng Part B Rev;* 16, 305-329, 2010]. In comparison with the surgical sealants such as BioGlue [CryoLife: BioGlue® *Summary of Safety and Effectiveness Surgical Adhesive Indications for Use Contraindications*; FDA Rep 2013], ProGel [ProGel summary of Safety and Effectiveness Data; FDA Rep 2008:1-26], and Crosseal [Crosseal Summary of Safety and Effectiveness Data; FDA Rep 2010], PASGel is more elastic and more mechanically robust. Both of these mechanical performances are important for internal and external wound dressing and tissue regeneration.

Feasibility of Using PASGel to Prevent Bleeding

A study was undertaken to see, inter alia, whether PASGel could be potentially used as:
- an internal bleeding sealant, surgical sealant for deep tissues; and/or
- a physical coagulant intended to be used to prevent blood leakage by filling or physical containment of a defect site.

Figure 6:
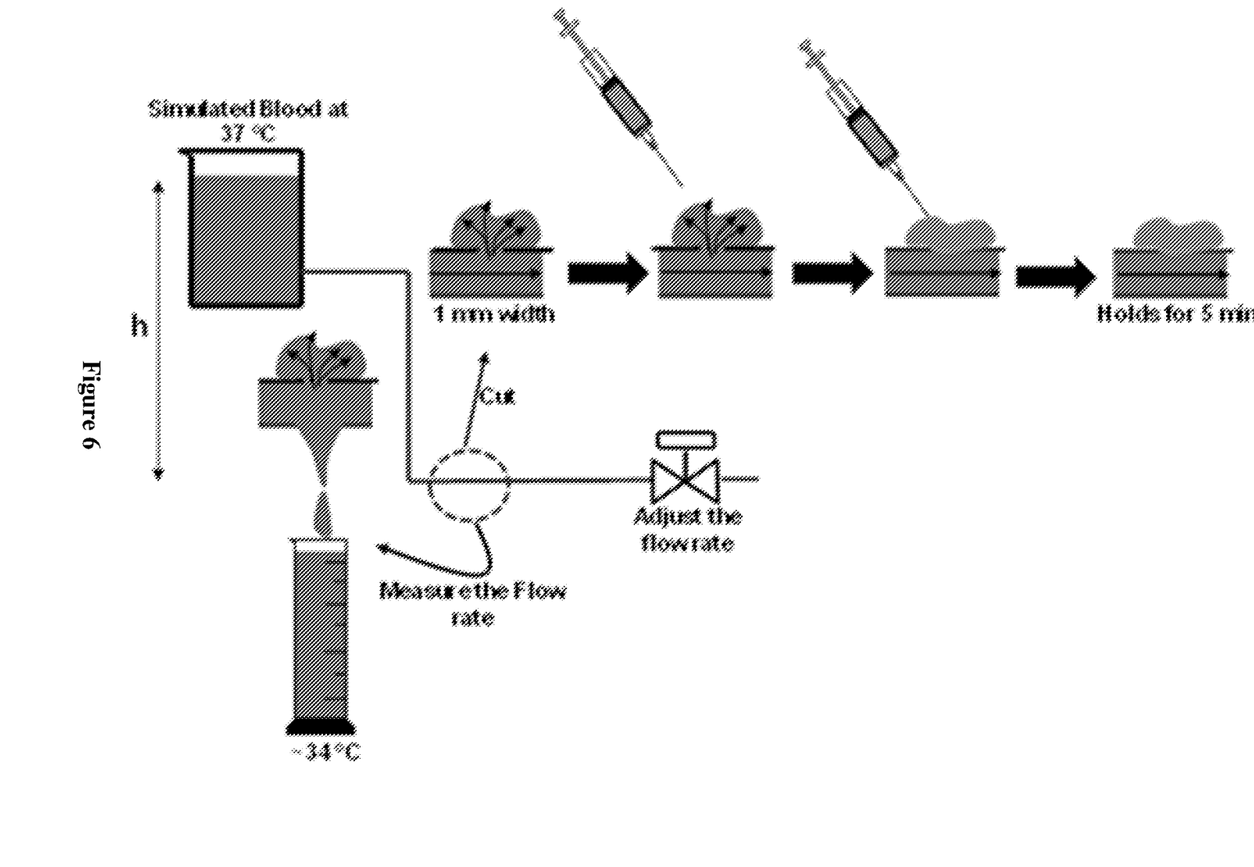
FIG. 6 shows a schematic for apparatus used to conduct a feasibility study to determine whether a PASGel system can prevent bleeding in a subject. The letter "h" denotes the variable to adjust the pressure in the system.

A schematic of the apparatus used to determine the feasibility of using PASGel to prevent bleeding is shown in FIG. 6. The Applicants developed the apparatus to confirm the feasibility of using PASGel to physically cope with this positive blood pressure and the blood flow. In this model the blood positive pressure at an internal defected site was nearly 33 mm Hg (=450 mm H$_2$O) and the flow rate was 3.7 ml/min to 50.3 ml/min (Tøndevold & Eliasen, 1982). The following parameters were used: tubing with a diameter of 1 cm, the Reynolds Number was 42297 (Turbulent), a valve was used to adjust the flow rates and the temperature of the "surgery" was ca. 34° C.

A model formulation of PASGel was prepared by conjugating a PAS polymer (with the formulation of 75% NIPAAm, 3 mol % PLA/HEMA with lactate length of 3, 2 mol % OEGMA, 14 mol % NAS and 6 mol % Salicylic acid) with GRGDS as a model peptide). The results displayed in Table 3, show that at the harshest condition (either highest flow rate or highest hydraulic pressure) the tested PAS Gel formulation can physically stop the flow of blood for nearly 5 minutes, sufficient time for the natural formation of blood clot and haemostasis. This result confirmed the high potential of the developed biomaterial for wound dressing and surgical sealant.

TABLE 3

The application of PASGel to stop simulated blood flow at different pressure sand flow rates.

| Pressure | Flow Rate (ml/min) | Period of No Flow (min) |
|---|---|---|
| 99 mm Hg (~1.5 m H$_2$O) | 10 | >15 |
| 99 mm Hg (~1.5 m H$_2$O) | 35 | ~8 |
| 99 mm Hg (~1.5 m H$_2$O) | 50 | ~5 |
| 33 mm Hg (~0.5 m H$_2$O) | 50 | ~5 |
| 76 mm Hg (~1 m H$_2$O) | 50 | ~5 |
| 99 mm Hg (~1.5 m H$_2$O) | 50 | ~5 |

INDUSTRIAL APPLICABILITY

In respect of potential commercial application, the present invention appeals as an off-shelf adhesive thermosetting biomaterial with intrinsic anti-inflammatory properties. These properties, in turn, give rise to applications such as a surgical sealant, wound healing dressing, filler and in vivo tissue regeneration scaffold.

Other commercial forms of the invention may include a ready to use liquid (PAS Gel in solution form needs to be stored at 4° C. with shelf life of 6-12 months) and long lasting powders, in which lyophilised polymer powder and physiological saline solution are provided separately. The kit would be ready to use by mixing the two parts for 4 hours at 4° C. This kit may have longer shelf-life (e.g., two years) and there would be no need for cool storage conditions.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A polymer consisting of:
    at least one antiseptic monomeric unit comprising a methacrylic ester derivative of salicylic acid selected from 2-hydroxy-5-N-methacrylamidobenzoic acid (5-HMA), 2-hydroxy-4-N-methacrylamidobenzoic acid (4-HMA), and a combination thereof;
    a water-soluble monomeric unit in the form of an oligo (ethylene glycol) methyl ether methacrylate (OEGMA) moiety;
    a mechanical strength-conferring monomeric unit in the form of polylactide-co-2-hydroxy-ethylmethyl acrylate (PLA/HEMA);
    a protein/polysaccharide-reactive monomeric unit in the form of an N-acryloxysuccinimide (NAS) moiety; and
    a thermosetting monomeric unit in the form of an N-isopropyl acrylamide (NIPAAm) moiety.

2. The polymer according to claim 1, comprising, in approximate relative molar proportions, less than about 5 mol % OEGMA.

3. The polymer according to claim 1, comprising, in approximate relative molar proportions, greater than about 8 mol % PLA/HEMA.

4. The polymer according to claim 1, comprising, in approximate relative molar proportions, NIPAAm (68 mol %); NAS (14 mol %); PLA/HEMA (8 mol %); OEGMA (5 mol %); and 5-HMA and/or 4-HMA (5 mol %).

5. A medical kit, said kit comprising a polymer as defined according to claim 1; instructions for combining the polymer with a biologically-compatible hydrogel; and optionally a syringe.

* * * * *